(12) United States Patent
Linder et al.

(10) Patent No.: US 8,540,512 B2
(45) Date of Patent: Sep. 24, 2013

(54) DENTAL IMPLANT SYSTEM

(75) Inventors: Andreas Linder, Basel (CH); Daniel Günter, Waldenburg (CH); Melanie Heyden, Mettmenstetten (CH)

(73) Assignee: Straumann Holding AG, Basel (CH)

( * ) Notice: Subject to any disclaimer, the term of this patent is extended or adjusted under 35 U.S.C. 154(b) by 438 days.

(21) Appl. No.: 11/273,466

(22) Filed: Nov. 14, 2005

(65) Prior Publication Data
US 2006/0105296 A1 May 18, 2006

(30) Foreign Application Priority Data
Nov. 16, 2004 (EP) .................................. 04027177

(51) Int. Cl.
*A61C 8/00* (2006.01)
(52) U.S. Cl.
USPC .......................................... 433/172; 433/173
(58) Field of Classification Search
USPC ...................................... 433/172–176, 201.1
See application file for complete search history.

(56) References Cited

U.S. PATENT DOCUMENTS

| | | | | |
|---|---|---|---|---|
| 5,116,225 A | * | 5/1992 | Riera | 433/173 |
| 5,281,140 A | * | 1/1994 | Niznick | 433/172 |
| 5,368,483 A | * | 11/1994 | Sutter et al. | 433/173 |
| 5,685,714 A | * | 11/1997 | Beaty et al. | 433/172 |
| 5,759,036 A | * | 6/1998 | Hinds | 433/214 |
| 6,152,737 A | | 11/2000 | Beaty et al. | |
| 6,500,003 B2 | * | 12/2002 | Nichinonni | 433/173 |
| 6,726,480 B1 | | 4/2004 | Sutter | |
| 2002/0076673 A1 | * | 6/2002 | Wagner et al. | 433/173 |
| 2006/0014120 A1 | * | 1/2006 | Sapian | 433/173 |

FOREIGN PATENT DOCUMENTS

| | | |
|---|---|---|
| DE | 198 50 097 A1 | 5/2000 |
| EP | 1 269 932 A | 1/2003 |
| EP | 1269932 * | 1/2003 |

* cited by examiner

*Primary Examiner* — Yogesh Patel
(74) *Attorney, Agent, or Firm* — Scully, Scott, Murphy & Presser, P.C.

(57) ABSTRACT

An abutment for dental implant systems of the kind suitable to be associated to a dental implant. The abutment has an inlay, and the inlay is provided at its upper part with an external profile having one or more shoulders for connecting and permanently jointing the inlay to the abutment. Further, the inlay may be shaped such that it is completely surrounded by the abutment in the assembled state of the dental implant system.

20 Claims, 3 Drawing Sheets

DENTAL IMPLANT SYSTEM

The present invention relates in general to an abutment for a dental implant system and in particular to a healing or a temporary abutment for a dental implant system.

As known to those expert in the field, in the reconstruction of missing or lost teeth, a dental implant is inserted in and secured to the patient's jawbone.

After a dental replacement by means of such an artificial dental implant has occurred, a healing period has to be observed in order to allow a correct osseo-integration of the dental implant in the bone tissue. Further, a sufficient healing time span must be provided for the surgical wound of the bone and the gingival tissues. In order to allow the completion of the healing process, a provisional head member, commonly called abutment, is mounted on the dental implant. Generally, abutments may be of healing type, so that only a healing function is provided without transmitting a load to the portion underlying the abutment, or of the temporary (or provisional) type, wherein, in addition to the healing function, the abutment supports a temporary crown or the like. Such a healing or temporary abutment should be easily removed at the end of the healing period so that the temporary abutment can be replaced with the definitive dental prosthesis, which has been manufactured in the meantime.

BACKGROUND OF THE INVENTION

The dental restoration of a partially or wholly edentulous patient with an artificial dentition is typically done in two stages. In the first stage, an incision is made through the gingiva to expose the underlying bone. An artificial tooth root, usually a threaded dental implant, is placed in the jawbone for integration. The threaded dental implant generally includes a threaded bore to receive a retaining screw holding mating components therein. During the first stage, the gum tissue overlying the implant is sutured and heals as the osseo-integration process continues.

Once the osseo-integration process is complete, a second stage is initiated. Here, the gum tissue is re-opened to expose the end of the threaded dental implant. A healing abutment or a temporary abutment is fastened to the exposed end of the threaded dental implant to allow the gum tissue to heal there around. Preferably, the gum tissue heals such that the aperture that remains generally approximates the size and contour of the aperture that existed around the natural tooth that is being replaced. To accomplish this, the abutment attached to the exposed end of the threaded dental implant has the same general contour as the gingival portion of the natural tooth being replaced. During the typical second stage of dental restoration, the abutment is removed and an impression coping is fitted onto the exposed end of the implant. This allows an impression of the specific region of the patient's mouth to be taken so that an artificial tooth is accurately constructed.

More recently, a single stage dental restoration is also being employed, wherein a healing abutment or a temporary abutment is fixed on the threaded dental implant immediately following the placement of the implant in the jaw bone.

The healing abutment or the temporary abutment is generally screwed to the implant realizing a coupling which can result to be unreliable and not steady, particularly when the coupling part of the abutment with a titanium dental implant is made of ceramics or plastic material. Similar drawbacks also apply to a non-provisional abutment.

A coupling between a threaded titanium dental implant and a permanent ceramic abutment including an intermediate element therebetween made of titanium is known from EP 1 269 932 A1. The object of EP 1 269 932 A1 is the provision of an anti-rotation lock between dental implant and the intermediate element, such that the known arrangement may sustain larger forces, which act with different eccentricity on the dental prosthesis carried by the permanent abutment. To this end, anti-rotation means are provided on the intermediate element and on the dental implant, thus ensuring a positive lock between the intermediate element and the dental implant when a connection screw is tightened at one end into a specially designed hole provided axially inside the dental implant, while at its other end the screw head retains the ceramic abutment against the intermediate element.

The implant system disclosed by the prior art of EP 1 269 932 A1 leaves unsolved several technical problems and suffers some drawbacks.

In fact, in general, the above prior art implant system does not allow to provide for a satisfactory coupling between the intermediate element and the abutment. Also the force distribution and force transmission from the abutment to the implant suffers drawbacks.

In addition, the positioning of the intermediate element with respect to the abutment and the dental implant is difficult.

Further, a separate intermediate element is difficult to manufacture and entails additional costs, which are not desirable, in particular in respect to healing abutments or temporary abutments.

Moreover, in some cases, when for instance the implant is inserted into a biologically aggressive environment, a further problem may arise, as the known intermediate element has a surface which faces outward and the intermediate element outside surface is specially designed in order to be in contact with the gum tissue or with the gum-tissue/jawbone interface. Due to the design of the intermediate element, the prior art implant system presents two interfaces facing outward to the natural tissues: the first interface is at the abutment-intermediate element interface, the second interface is the intermediate element-dental implant interface. It is known to the experts in the art, that the implant systems are normally inserted into a biologically aggressive environment, and so implant interfaces are a point of possible microbiological attack, being rather impossible to precisely realize the joint between the various elements.

SUMMARY OF THE INVENTION

The aim of the present invention is to provide a dental implant system suitable to support an abutment, in particular a temporary abutment or a healing abutment, which eliminates or reduces the drawbacks of known dental implant systems.

In particular, it has been found that by means of an inlay integral with the abutment and made of materials with higher mechanical characteristics with respect to the material of the abutment, which is for instance made of plastic materials or ceramics, a better force distribution as well as force transmission from the abutment to the implant is achieved, and furthermore an enforcement of the whole construction is obtained.

Moreover, the inlay should be realized with a material which is better compatible with the material of the implant. Due to the above mentioned consideration the inlay of the present invention is preferably made of titanium or titanium alloys, gold, ceramic, reinforced plastic material, composite fibers or any material, in particular metal alloy with suitable material characteristics.

Furthermore, it has also been found that employing an titanium inlay integral with a plastic or ceramic abutment the mechanical strength and finally the durability of the abutment results to be increased in comparison with a traditional implant system not provided with such a titanium inlay.

Within the scope of this aim, an object of the present invention is to provide a dental implant system which allows to support a provisional abutment or a healing abutment or also non-provisional abutments.

Another object of the invention is to provide an implant system provided with an inlay which does not face outward, in order to reduce the number of the implant interfaces facing to the natural tissues.

Another object is to provide an implant system suitable to realize an optimized gingival-former action. In fact, a provisional or healing abutment serves as a gingival-former to shape the gum tissue during healing of provisionalisation.

This aim, these objects and other which will become better apparent hereinafter, are achieved by an implant system according to the appended claims.

BRIEF DESCRIPTION OF THE DRAWINGS

Further characteristics and advantages of the invention will become better apparent from the following description of a preferred but not exclusive embodiment of the implant system according to the invention, illustrated by way of non-limitative example in the accompanying drawings, wherein.

DESCRIPTION OF THE PREFERRED EMBODIMENTS

The implant system of the present invention comprises a dental implant, e.g. a conventional threaded dental implant, an abutment, which can be of the provisional or healing type, an inlay (in particular a titanium or titanium alloy inlay) and a connection screw. However, the person skilled in the art will readily appreciate that the present invention is not limited to the above type of abutment and indeed can be implemented with any kind of abutments.

Figure 1:
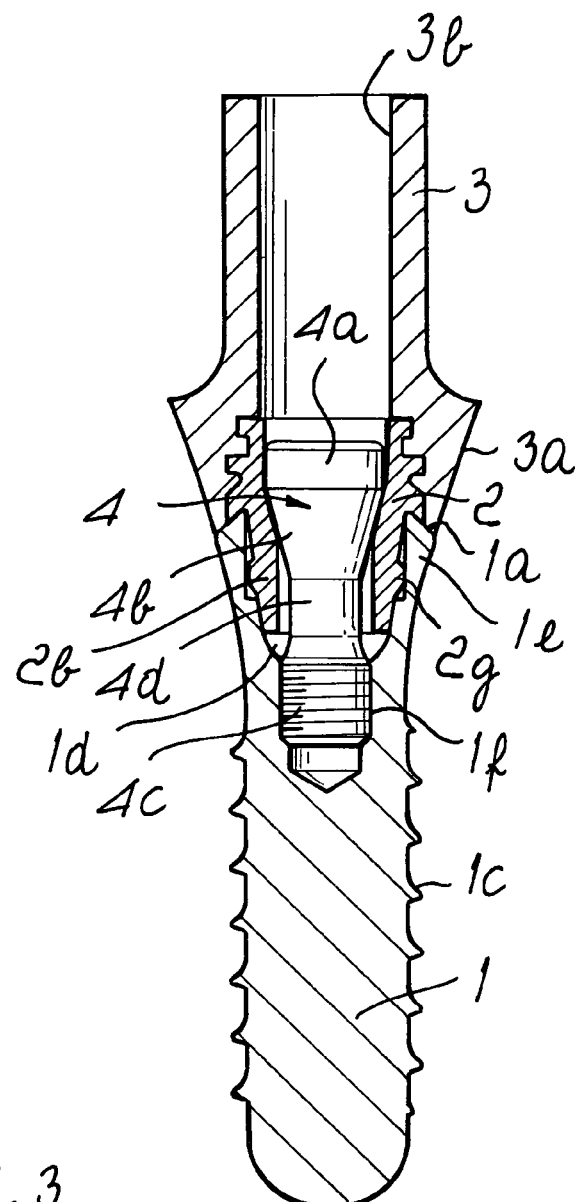
FIG. 1 is a cross-sectional view of the system of the present invention according to a first embodiment implemented as a provisional abutment.
Figure 3:
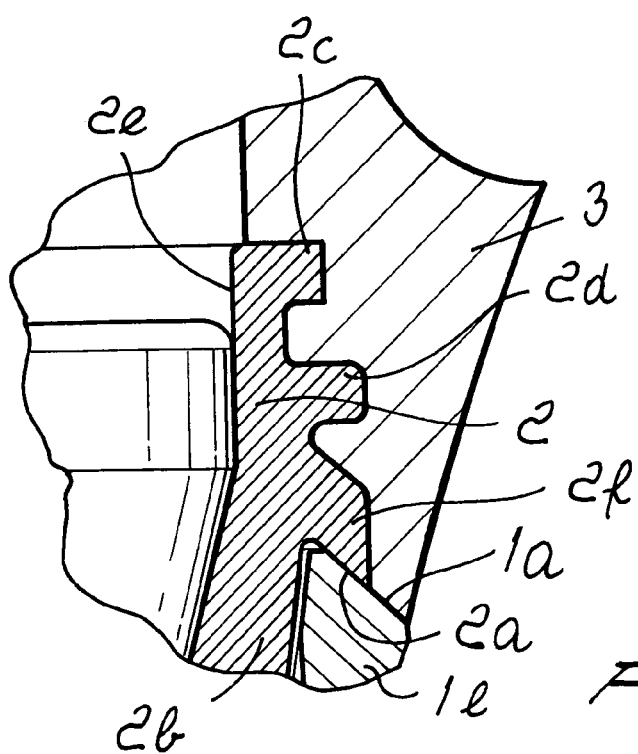
FIG. 3 is a particular of the cross-sectional view of FIG. 1, showing in detail the abutment-inlay-dental implant interface, wherein the inlay is substantially not laterally visible in the assembled state of the implant system.

With reference to FIG. 1, the implant system comprises a conventional dental implant 1, which may be for example a conventional substantially cylindrical or tapered implant having a threaded portion 1c surrounding an external cylindrical or tapered body, this threaded portion 1c being suitable to be screwed in the bone tissue. The dental implant 1 further comprises a neck portion 1e, which can interact with the bone-gingival tissue interface once the dental implant 1 will be positioned in its final seat in the bone tissue. This neck portion 1e ends upwardly with an upper surface 1a. Such implant design is well known to those skilled in the art. Upwardly the upper surface 1a of the dental implant 1 contacts, as shown in FIG. 3, a contacting surface 2a of the inlay 2, the inlay 2 being inserted with its bottom portion 2b into the dental implant 1. More in detail, the bottom portion 2b is inserted into a cavity 1d of the dental implant 1, which is specially designed in order to fit to the external profile of the bottom portion 2b of the inlay 2. The inlay 2 should have an upper part with an external profile provided with means for connecting and permanently jointing said inlay 2 to the temporary abutment 3, said means comprising one or more shoulders, e.g. a first upper shoulder 2c and/or a second median shoulder 2d, in order to steadily retain the inlay 2 inside the abutment 3 in a coaxial position. According to the invention, the abutment 3 is molded around the first upper shoulder 2c and the second median shoulder 2d, such that an integral structure between the abutment 3 and the inlay 2 is implemented. The molding can be achieved by plastic injection molding, ceramic injection molding and the like according to the material of the abutment. It is also conceivable to mold the inlay 2, in particular an inlay made from titanium alloy, by means of injection molding into the abutment 3.

The inlay 2 is further provided with anti-rotational means, e.g. a polygonal element 2g, and the dental implant 1 is, in its internal cavity, provided with complementary cavities suitable to exactly meet the external profile of the inlay 2, and thus rotationally secure the inlay-abutment combination. The inlay 2, as shown in FIGS. 1 and 3, results to be inserted into the dental implant 1 with its bottom part 2b, while at an upper region it is provided with a downward facing shoulder 2f on which is realized the contacting surface 2a suitable to abut on the upper surface 1a of the neck portion 1e of the dental implant 1. As per FIG. 1, the abutment 3 with the integral inlay 2 is retained against the implant 1 through a connection screw 4 having a proximal head-portion with a cylindrical portion 4a and a tapered portion 4b suitable to fit a counter-shaped internal cavity 2e of the inlay 2, and a distal threaded portion 4c adapted to be screwed in a threaded hole 1f provided axially inside the dental implant 1.

Figure 4:
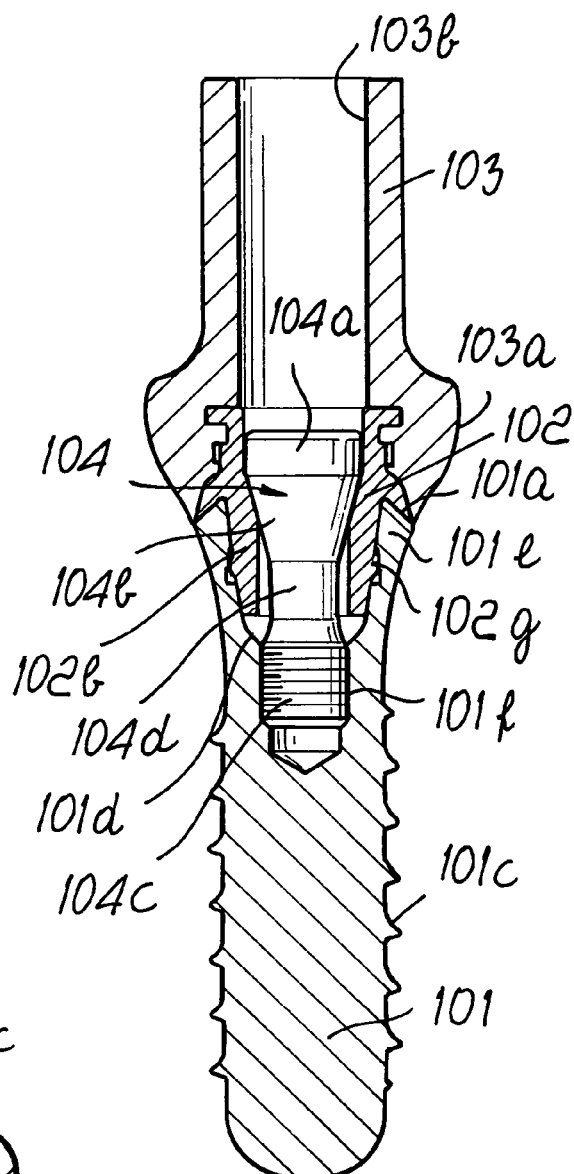
FIG. 4 is a cross-sectional view of the system of the present invention according to a second embodiment again implemented as a provisional abutment.

The provisional abutment 3 shown in FIG. 1 may be provided with an emergence profile 3a, which serves as gingival former, being suitable to shape the gum tissue during healing or provisionalisation. This part can be modified in order to obtain different modifications of the gum tissue. As an example, the FIG. 4 shows a different embodiment of the abutment in which the emergence profile 103a has a rounded shape. Due to the rounded shape of the emergence profile of the abutment, it is possible to obtain a reduced gum growth around the implant site even with an implant with the same diameter of the neck portion. It has been also been found that it is particularly advantageous to provide the abutment with an emergence profile that may be customized by a dental surgeon or a dental technician otherwise in accordance with the topology of the implant site of a particular patient.

Figure 3A:
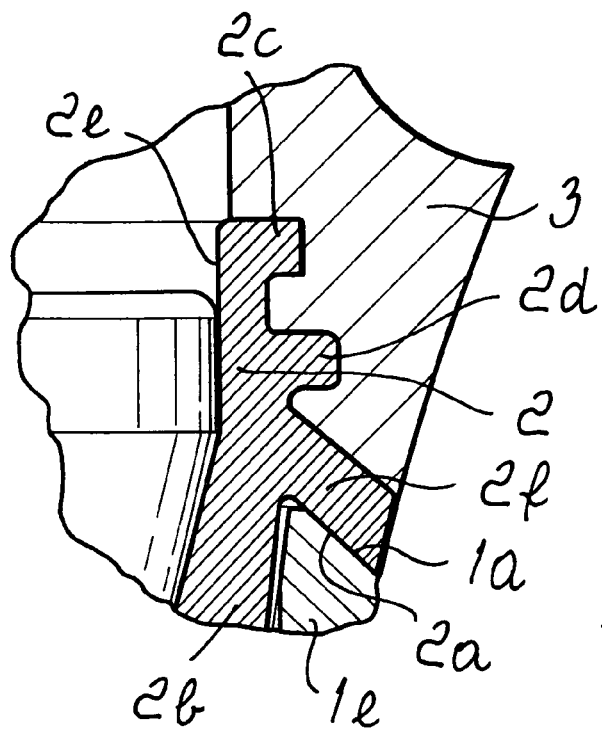
FIG. 3a is a variation of the cross-sectional view of FIG. 3, showing in detail the abutment-inlay-dental implant interface, wherein the inlay is laterally visible in the assembled state of the implant system.

FIG. 3a is a variation of the first embodiment of FIG. 1 where the inlay 2 is visible laterally in the assembled state of the implant system. This variation may be used in a biologically non-aggressive environment and provides for an even further improved force distribution as the contacting surface between the inlay and the dental implant is maximized. Otherwise all details of FIG. 3a are identical to FIG. 1 and will therefore be omitted.

Figures 7A, 7B:
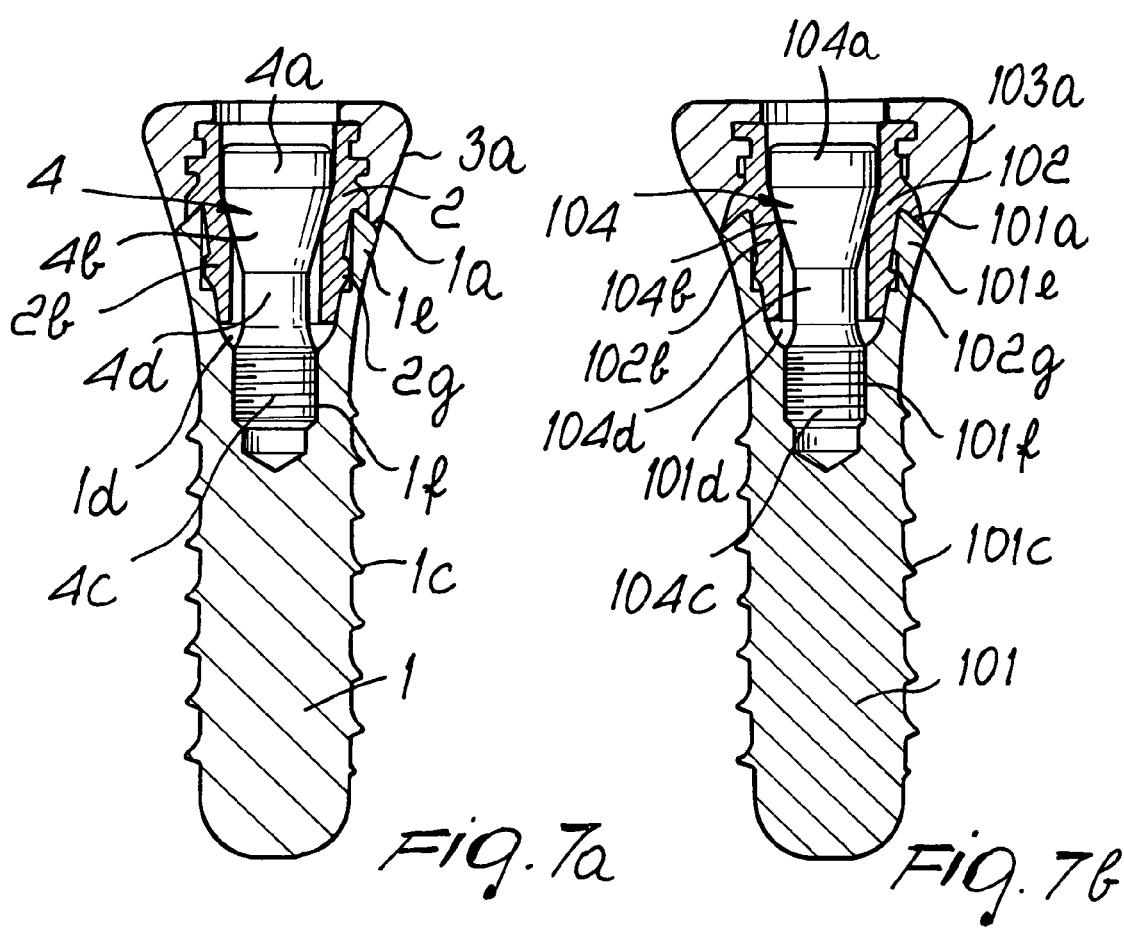
FIG. 7a is a variation of the first embodiment of FIG. 1 implemented as a healing abutment.
FIG. 7b is a variation of the second embodiment of FIG. 4 implemented as a healing abutment.

Also FIG. 7a is a variation of the first embodiment of FIG. 1 implemented as a healing abutment. Otherwise, again, all details of FIG. 7a are identical to FIG. 1 and will therefore be omitted. The healing abutment may be manufactured to be smaller sized as shown in FIG. 7a or may be processed in situ by the dental technician or dental surgeon from a larger sized abutment to a smaller size.

Figure 2:
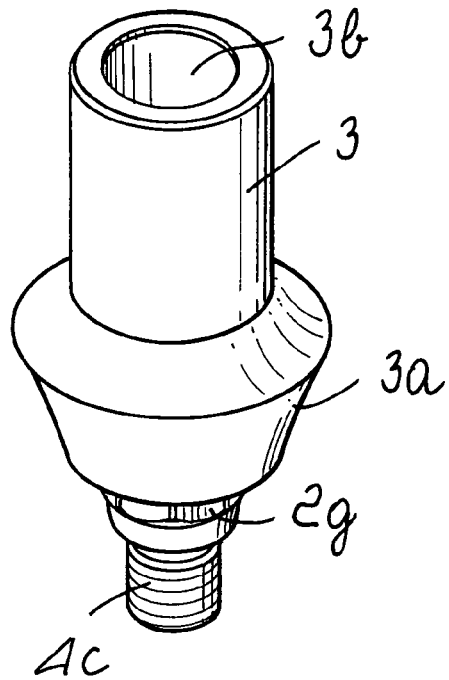
FIG. 2 is a prospective view of the abutment and of the inlay according to the first embodiment of the present invention assembled together.
Figure 5:
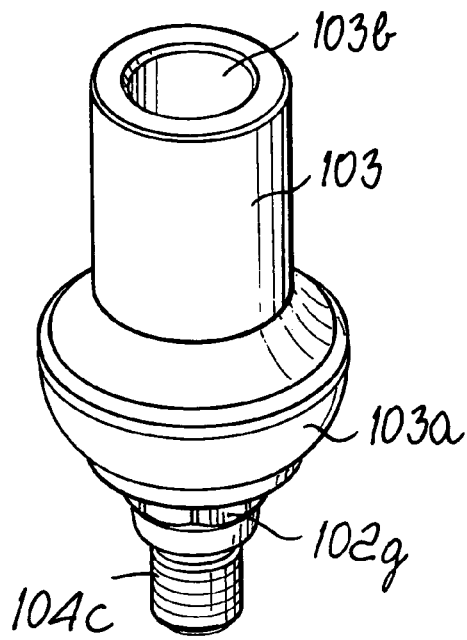
FIG. 5 is a prospective view of the abutment and of the inlay according to the second embodiment of the present invention assembled together.
Figure 6:
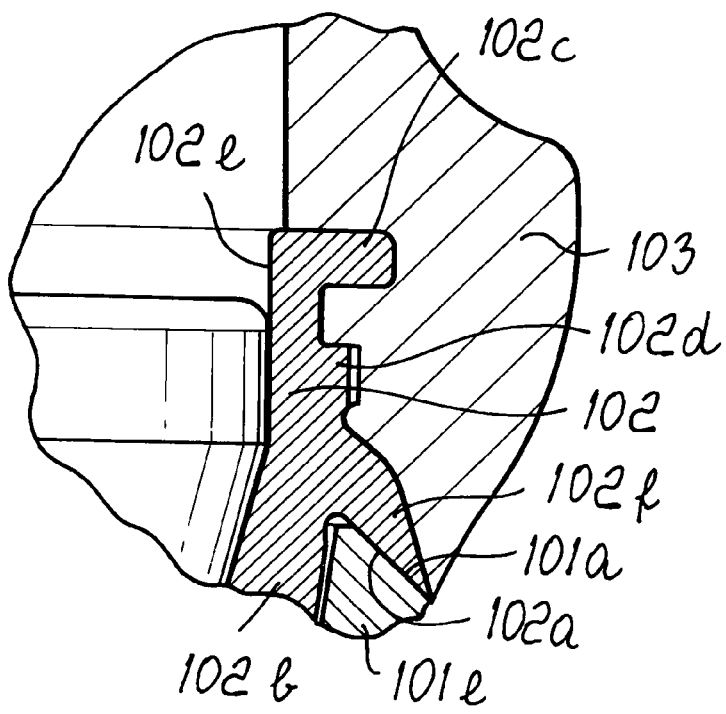
FIG. 6 is a particular of the cross-sectional view of FIG. 4, showing in detail the abutment-inlay-dental implant interface.

FIGS. 4 to 6 show a second embodiment of the implant system according to the present invention, wherein generally the single parts are corresponding to those of FIGS. 1 to 3 and therefore the detailed description thereof has been omitted. It is noted that the reference numerals are augmented by 100 as compared to FIGS. 1 to 3.

Varying from FIGS. 1 to 3, FIG. 6 shows that the inlay 102 could have different profiles in order to improve the stability of the interfaces inlay-abutment and inlay-dental implant. In particular, in this second embodiment, the inlay 102 has a downward-facing shoulder 102f, which entirely overlaps the upper surface 101a of the neck portion 101e of the implant 101. The cross-sectional view of FIG. 6 shows the tapered shape of the shoulder 102f.

As above mentioned, the presence of the integral inlay 102 interposed between the abutment 103 and the dental implant 101 enforces the whole construction of the implant system and serves for a better force distribution as well as force transmission into the dental implant 101. Further, it seems that the second embodiment of the inlay 102 completely overlapping the dental implant upper surface 101a and having a greater contacting surface 102a also provides for a further improvement in the force distribution.

FIG. 7b is a variation of the second embodiment of FIG. 4 implemented as a healing abutment. Otherwise, all details of FIG. 7b are identical to FIG. 4 and will therefore be omitted. As mentioned in conjunction with FIG. 7a the healing abutment of FIG. 7a may also be manufactured to have a smaller size or may be processed in situ from a larger sized abutment.

It has thus been shown that the present invention fulfills the proposed aim of providing an implant system which allows to steadily retain an abutment jointed to a dental implant.

Moreover, the presence of the integral inlay allows achieving a higher mechanical strength of the whole dental implant system of the invention, the durability of the abutment finally resulting longer in comparison with traditional dental implant systems.

Another aim of the present invention is to allow the possibility of employing a shortened abutment, which can therefore act as a healing abutment, instead of the provisional abutment. In order to achieve this aim, the inlay has been specially designed as discussed above.

Further, it has been shown that the present invention as described fulfills the proposed object of reducing the number of implant interfaces facing to natural tissues, providing an implant system in which the inlay does not have perimetral surfaces facing in a lateral direction.

Moreover, the present invention fulfills the aim of providing an implant system with an abutment characterized by the presence of an emergence profile, which could be differently shaped in order to modify the gingival shape according to the clinical situation.

The present invention is also advantageous over EP 1 269 932 A1 in that the connection screw is positioned at a very low position within the abutment. Therefore it is possible to safely remove the upper part of the abutment, which is a particular advantage of the present invention if the abutment is shaped in situ.

Clearly, several modifications will be apparent to and can be readily made by the skilled in the art without departing from the scope of the present invention. Therefore, the scope of the claims shall not be limited by the illustrations or the preferred embodiments given in the description in the form of examples, but rather the claims shall encompass all of the features of patentable novelty that reside in the present invention, including all the features that would be treated as equivalents by the skilled in the art.

The disclosures in EPA 04027177.7 from which this application claims priority are incorporated herein by reference.

What is claimed is:

1. An abutment for dental implant systems suitable to be associated to a dental implant,
wherein the abutment comprises an inlay,
the inlay comprising:
an upper part having an external profile comprising means for connecting and permanently joining the inlay to the abutment;
a bottom part configured to be inserted into a neck portion of the dental implant; and
a downwardly facing shoulder extending radially away and downwardly from the upper part, configured for engaging an upper surface of the neck portion,
wherein the inlay is shaped such that said inlay is not visible laterally when said bottom part is inserted entirely into the neck portion of the dental implant.

2. The abutment according to claim 1, wherein the abutment is molded around the means for connecting and permanently jointing, or wherein the means for connecting and permanently jointing are molded into the abutment.

3. The abutment according to claim 1, wherein the means for connecting and permanently jointing the inlay to the abutment comprises a plurality of shoulders interspaced by sections of the inlay having a smaller diameter than that of the shoulders.

4. The abutment according to claim 1, wherein said downward facing shoulder comprises a contacting surface suitable to abut on an upper surface of a neck portion of the dental implant.

5. The abutment according to claim 4, wherein the contacting surface of the downward facing shoulder completely overlaps the upper surface of the dental implant.

6. The abutment according to claim 4, wherein the contacting surface of the downward facing shoulder partially overlaps the upper surface of the dental implant.

7. The abutment according to claim 1, wherein the abutment is a provisional abutment or a healing abutment, and/or wherein the abutment has an emergence profile.

8. The abutment according to claim 7, wherein the emergence profile is either customizable by a dental surgeon or conforms the topology of the implant site of a particular patient.

9. The abutment according to claim 1, wherein the downward facing shoulder of the inlay has a lateral edge which is parallel to a longitudinal axis of the abutment.

10. The abutment of claim 9, wherein the lateral edge of the downward facing shoulder of the inlay is spaced from the exterior surface of the abutment.

11. The abutment according to claim 1, wherein the downward facing shoulder of the inlay has a lateral edge which is inclined in respect to a longitudinal axis of the abutment.

12. The invention according to claim 1, wherein the inlay is made of a material, which has higher mechanical characteristics with respect to the mechanical characteristics of the abutment to which said inlay is coupled.

13. The invention according to claim 12, wherein the abutment is made of plastic or ceramic materials and said inlay is made of titanium, titanium alloys, steel, gold, ceramic, reinforced plastic material or also composite fibers.

14. A dental implant system comprising a dental implant, an abutment and a connection screw suitable to steadily join the abutment and the dental implant together,
   wherein the dental implant system further comprises an inlay insertable within a neck portion of the dental implant, and
   wherein the inlay comprises an upper part having an external profile comprising means for connecting and permanently joining the inlay to the abutment, a bottom part configured to be inserted into the neck portion of the dental implant, and a downward facing shoulder extending radially away and downwardly from the upper part and being configured for engaging an upper surface of the neck portion, the inlay being shaped such that said inlay is not visible laterally when said bottom part is inserted entirely into the neck portion of the dental implant.

15. The dental implant system according to claim 14, wherein the inlay has a bottom part provided with anti-rotational means.

16. The dental implant system according to claim 15, wherein the anti-rotational means comprise a polygonal element.

17. The dental implant system according to claim 14, wherein the means for connecting and permanently jointing the inlay to the abutment comprises a plurality of shoulders interspaced by sections of the inlay having a smaller diameter than that of the shoulders.

18. The dental implant system according to claim 14, wherein the abutment is a provisional abutment or a healing abutment, and/or wherein the abutment has an emergence profile.

19. The dental implant system according to claim 18, wherein the emergence profile is customizable by a dental surgeon or conforms the topology of the implant site of a particular patient.

20. A dental implant system comprising a dental implant, an abutment and a connection screw suitable to steadily join the abutment and the dental implant together,
   wherein the dental implant system further comprises an inlay insertable within a neck portion of the dental implant,
   wherein the inlay is completely included inside the dental implant system and laterally invisible, so that no part of the inlay faces the natural tissues surrounding the implant, and
   wherein the inlay comprises an upper part having an external profile comprising means for connecting and permanently joining the inlay to the abutment, a bottom part configured to be inserted into the neck portion of the dental implant, and a downward facing shoulder extending radially away and downwardly from the upper part and being configured for engaging an upper surface of the neck portion.

* * * * *